(12) United States Patent
Hashimshony et al.

(10) Patent No.: US 8,147,423 B2
(45) Date of Patent: Apr. 3, 2012

(54) TISSUE-CHARACTERIZATION SYSTEM AND METHOD

(75) Inventors: Dan Hashimshony, Givat Ada (IL); Gal Aharonowitz, Moshav Gan Haim (IL); Gil Cohen, Jerusalem (IL); Iddo Geltner, Herzlia (IL)

(73) Assignee: Dune Medical Devices, Ltd., Caesarea (IL)

( * ) Notice: Subject to any disclaimer, the term of this patent is extended or adjusted under 35 U.S.C. 154(b) by 426 days.

(21) Appl. No.: 11/712,529

(22) Filed: Mar. 1, 2007

(65) Prior Publication Data

US 2008/0214953 A1    Sep. 4, 2008

(51) Int. Cl.
*A61B 10/00* (2006.01)
(52) U.S. Cl. ........................... 600/562; 600/587
(58) Field of Classification Search .............. 600/562, 600/552
See application file for complete search history.

(56) References Cited

U.S. PATENT DOCUMENTS

| | | |
|---|---|---|
| 3,830,224 A | 8/1974 | Vanzetti et al. |
| 4,291,708 A | 9/1981 | Frei et al. |
| 4,344,440 A | 8/1982 | Aaby et al. |
| 4,458,694 A | 7/1984 | Sollish et al. |
| 4,537,203 A | 8/1985 | Machida |
| 4,539,640 A | 9/1985 | Fry et al. |
| RE32,000 E | 10/1985 | Sagi |
| 4,617,939 A | 10/1986 | Brown et al. |
| 4,625,171 A | 11/1986 | Sekihara et al. |
| 4,682,594 A | 7/1987 | Mok |
| 4,689,567 A | 8/1987 | Maudsley |
| 4,751,464 A | 6/1988 | Bridges |
| 4,768,513 A | 9/1988 | Suzuki |
| 4,785,806 A | 11/1988 | Deckelbaum |
| 5,115,137 A | 5/1992 | Andersson-Engels et al. |
| 5,143,079 A | 9/1992 | Frei et al. |
| 5,227,730 A | 7/1993 | King et al. |
| 5,261,825 A | 11/1993 | Chaves |
| 5,442,290 A | 8/1995 | Crooks |
| 5,482,041 A | 1/1996 | Wilk et al. |
| 5,558,092 A | 9/1996 | Unger et al. |
| 5,572,132 A | 11/1996 | Pulyer et al. |
| 5,630,426 A | 5/1997 | Eggers et al. |

(Continued)

FOREIGN PATENT DOCUMENTS

DE    3637549 A1    5/1988

(Continued)

OTHER PUBLICATIONS

PCT Invitation to Pay Additional Fees and Communication Relating to the Results of the Partial International Search.

(Continued)

*Primary Examiner* — Max Hindenburg
*Assistant Examiner* — Renee Danega
(74) *Attorney, Agent, or Firm* — Browdy and Neimark, PLLC (57) ABSTRACT

A measurement system and method are provided for use in characterizing a tissue. The system comprises a probe adapted for operating in either a scan mode or a measure mode, and a control unit for operating the probe. The probe comprises a sensing module for measuring one or more parameters indicative of one or more states of the tissue; and an attachment module configured and operable to enable selective operation of the probe in either one of the scan mode and the measure modes. The control unit is configured and operative to selectively operate the probe in either one of the scan and measure modes.

35 Claims, 7 Drawing Sheets

U.S. PATENT DOCUMENTS

| | | | |
|---|---|---|---|
| 5,704,355 | A | 1/1998 | Bridges |
| 5,727,569 | A | 3/1998 | Benetti et al. |
| 5,735,278 | A | 4/1998 | Hoult et al. |
| 5,744,971 | A | 4/1998 | Chan et al. |
| 5,758,646 | A | 6/1998 | Van Der Meulen et al. |
| 5,800,350 | A | 9/1998 | Coppleson et al. |
| 5,807,257 | A | 9/1998 | Bridges |
| 5,810,742 | A | 9/1998 | Pearlman |
| 5,821,410 | A | 10/1998 | Xiang et al. |
| 5,829,437 | A | 11/1998 | Bridges |
| 5,884,239 | A | 3/1999 | Romanik, Jr. |
| 5,900,618 | A | 5/1999 | Anlage et al. |
| 5,927,284 | A | 7/1999 | Borst et al. |
| 6,010,455 | A * | 1/2000 | Barnett et al. ............... 600/363 |
| 6,026,323 | A | 2/2000 | Skladnev et al. |
| 6,055,452 | A | 4/2000 | Pearlman |
| 6,061,589 | A | 5/2000 | Bridges et al. |
| 6,090,041 | A | 7/2000 | Clark et al. |
| 6,093,156 | A * | 7/2000 | Cunningham et al. ........ 600/573 |
| 6,109,270 | A | 8/2000 | Mah et al. |
| 6,135,968 | A | 10/2000 | Brounstein et al. |
| 6,167,297 | A | 12/2000 | Benaron |
| 6,173,604 | B1 | 1/2001 | Xiang et al. |
| 6,233,479 | B1 | 5/2001 | Haddad et al. |
| 6,258,576 | B1 | 7/2001 | Richards-Kortum et al. |
| 6,280,704 | B1 | 8/2001 | Schutt et al. |
| 6,287,302 | B1 | 9/2001 | Berube |
| 6,308,097 | B1 | 10/2001 | Pearlman |
| 6,315,981 | B1 | 11/2001 | Unger |
| 6,321,106 | B1 | 11/2001 | Lemelson |
| 6,331,166 | B1 | 12/2001 | Burbank et al. |
| 6,370,426 | B1 | 4/2002 | Campbell et al. |
| 6,375,634 | B1 | 4/2002 | Carroll |
| 6,377,841 | B1 | 4/2002 | Lin et al. |
| 6,397,095 | B1 | 5/2002 | Eyuboglu et al. |
| 6,405,733 | B1 | 6/2002 | Fogarty et al. |
| 6,500,112 | B1 | 12/2002 | Khouri |
| 6,530,944 | B2 | 3/2003 | West et al. |
| 6,546,787 | B1 | 4/2003 | Schiller et al. |
| 6,564,806 | B1 | 5/2003 | Fogarty et al. |
| 6,597,185 | B1 | 7/2003 | Talanov et al. |
| 6,671,540 | B1 | 12/2003 | Hochman |
| 6,677,755 | B2 | 1/2004 | Belt et al. |
| 6,695,782 | B2 | 2/2004 | Ranucci et al. |
| 6,699,206 | B2 | 3/2004 | Burbank et al. |
| 6,722,371 | B1 | 4/2004 | Fogarty et al. |
| 6,728,565 | B2 | 4/2004 | Wendlandt |
| 6,741,077 | B2 | 5/2004 | Yokoyama et al. |
| 6,747,454 | B2 | 6/2004 | Belt |
| 6,752,154 | B2 | 6/2004 | Fogarty et al. |
| 6,766,185 | B2 | 7/2004 | Scott |
| 6,813,515 | B2 | 11/2004 | Hashimshony |
| 6,840,948 | B2 | 1/2005 | Albrecht et al. |
| 6,909,084 | B2 | 6/2005 | Tachi et al. |
| 6,962,587 | B2 | 11/2005 | Johnson et al. |
| 7,082,325 | B2 | 7/2006 | Hashimshony et al. |
| 7,184,824 | B2 | 2/2007 | Hashimshony |
| 7,207,952 | B2 * | 4/2007 | Takinami et al. ............. 600/584 |
| 7,435,232 | B2 * | 10/2008 | Liebschner ................... 600/587 |
| 2001/0051774 | A1 | 12/2001 | Littrup et al. |
| 2002/0055754 | A1 | 5/2002 | Ranucci et al. |
| 2002/0059938 | A1 | 5/2002 | Fogarty et al. |
| 2002/0068810 | A1 | 6/2002 | Burbank et al. |
| 2002/0120265 | A1 | 8/2002 | Fowler |
| 2003/0045798 | A1 | 3/2003 | Hular et al. |
| 2003/0062897 | A1 | 4/2003 | Belt et al. |
| 2003/0117140 | A1 | 6/2003 | Belt et al. |
| 2003/0138378 | A1 | 7/2003 | Hashimshony |
| 2003/0171664 | A1 | 9/2003 | Wendlandt |
| 2003/0187366 | A1 | 10/2003 | Hashimshony |
| 2003/0199753 | A1 | 10/2003 | Hibner et al. |
| 2003/0229343 | A1 | 12/2003 | Albrecht et al. |
| 2004/0168692 | A1 | 9/2004 | Fogarty et al. |
| 2005/0010131 | A1 | 1/2005 | Burbank et al. |
| 2005/0021019 | A1 * | 1/2005 | Hashimshony et al. ........ 606/32 |
| 2005/0027209 | A1 * | 2/2005 | Eggers ........................... 600/564 |
| 2005/0107717 | A1 | 5/2005 | Yamamoto et al. |
| 2006/0063992 | A1 | 3/2006 | Yu et al. |
| 2006/0264738 | A1 | 11/2006 | Hashimshony et al. |

FOREIGN PATENT DOCUMENTS

| | | |
|---|---|---|
| WO | 97/12553 A1 | 4/1997 |
| WO | 01/43630 A2 | 6/2001 |
| WO | 0165240 A1 | 9/2001 |
| WO | 03060462 A2 | 7/2003 |
| WO | 2005009200 A2 | 2/2005 |
| WO | 2005089065 A2 | 9/2005 |
| WO | 2006072947 A2 | 7/2006 |
| WO | 2006092797 A2 | 9/2006 |
| WO | 2006103665 A2 | 10/2006 |
| WO | 2007015255 A2 | 2/2007 |

OTHER PUBLICATIONS

U.S. Appl. No. 60/641081, filed Jan. 4, 2005, D. Hashimshony.

V. Rajshekhar, "Continuous impedance monitoring during CT-guided stereotactic surgery: relative value in cycstic and solid lesions", British Journal of Neurosurgery, vol. 6, 1992, pp. 439-444.

Section on Biomedical Stochastic Physics (SBSP), "Subsurface Spectroscopy", http://www.sbsp-limb.nichd.nih.gov/html/spectroscopy.html. Apr. 1, 2005.

K. Harzbecker et al., "Thermogaphic thorax diagnostics", Z. Gesamte Inn. Med. Feb. 1978, 1;33(3):78-80 Abstract only (article in German).

Dexter Li, Kondat'ev VB., "Thermography in different diagnosis of lymphostasis in the lower limbs",Vestin Khir Im I. I Grek. Jun. 1976;116(6):60-4 Abstract only (article in Russian).

Ascension Products Ltd., MiniBIRD 500 & 800, downloaded on Mar. 15, 2005, http://www.ascension-tech.com/products/minibird.php.

D. Misra et al., "Noninvasive Electrical Characterization of Materials at Microwave Frequencies Using an Open-Ended Coaxial Line: Test of an Improved Calibration Technique", IEEE Transactions on Microwave Theory & Techniques, 38:(1):8-13, 1990.

E. Burdette et al., "In Vivo Probe Measurement Technique for Determining Dielectric Properties at VHF Through Microwave Frequencies", IEEE Transactions on Microwave Theory & Techniques, MTT-28(4):414-427, 1980.

Y. Xu et al., "Measurement of Microwave Permittivity Using Open Ended Elliptical Coaxial Probes", IEEE Transactions on Microwave Theory & Techniques, 40(1): 143-150, 1992.

M. Stuchly et al., "Measurement of Radio Frequency Permittivity of Biological Tissues with an Open-Ended Coaxial Line: Part II—Experminental Results", IEEE Transactions on Microwave Theory & Techniques, MTT-30(1): 87-91, 1982.

J. Mosig et al., "Reflection of an Open-Ended Coaxial Line and Application to Nondestructive Measurement Materials", IEEE Transactions on Instrumentation and Measurement, IM-30(1):46-51, 1981.

D. Smith et al., "In Vivo Measurement of Tumor Conductiveness with the Magnetic Bioimpedance Method", IEEE Transactions on Biomedical Engineering, vol. 47, No. 10, Oct. 2000.

L. G. Brown, "A Survey of Image Registration Techniques", ACM Computing Surveys, 24(4):325-376, 1992.

M. Beard et al., "Size-Dependent Photoconductivity in CdSe Nanoparticles as Measued by Time-Resolved Terahertz Spectroscopy", Nano Letters, 2(9), 983-987, Aug. 14, 2002, Abstract only.

M. Akerman et al., "Nanocrystal targeting in vivo", PNAS, 99(20), 12617-12621, Oct. 1, 2002.

A. J. Surowiec et al., "Dielectric Properties of Breast Carcinoma and the Surrounding Tissues", IEEE Transactions on Biomedical Engineering, vol. 35, No. 4, Apr. 1988.

H. P. Schwan, "Mechanisms responsible for electrical properties of tissues and cell suspensions", Medical Progress Through Technology, 19:163-165, 1993.

J. G. Proakis et al., "Digital Signal Processing: Principles, Algorithms, and Applications", Third Edition, Prentice Hall International Inc., Chapter 4, Table of Contents and cover page only.

"Affinity Biosensors: Techniques and Protocols", Edited by K.R. Rogers and A. Mulchandani, Humana Press, New Jersey, USA, 1998, Table of Contents page only.

Journal: Biosensors & Bioelectronics, vol. 20, Issue 8, pp. 1459-1695, Feb. 15, 2005, Table of Contents page only.
Journal: Biosensors & Bioelectronics, vol. 20, Issue 6, pp. 1029-1295, Dec. 15, 2004, Table of Contents page only.
Journal: Biosensors & Bioelectronics, vol. 20, Issue 5, pp. 917-1028, Nov. 15, 2004, Table of Contents pages only.
Journal: Biosensors & Bioelectronics, vol. 20, Issue 1, pp. 1-142, Jul. 30, 2004, Table of Contents pages only.
Journal: Biosensors & Bioelectronics, vol. 20, Issue 12, pp. 2387-2593, Jun. 15, 2005, Table of Contents pages only.
Journal: Sensors & Actuators B (Chemical), vol. 103, Issues 1-2, pp. 1-473, Sep. 29, 2004, Table of Contents pages only.
Journal: Sensors & Actuators B (Chemical), vol. 102, Issue 1, pp. 1-177, Sep. 2004, Table of Contents pages only.
Journal: Sensors & Actuators B (Chemical), vol. 106, Issue 1, pp. 1-488, Apr. 29, 2005, Table of Contents pages only.
Sensors: A Comprehensive Survey—vol. 2: Chemical and Biochemical Sensors, Part I, Edited by W. Goepel, J. Hesse, J. N. Zemel, (VCH, 1991), Table of Contents pages only.
Sensors: A Comprehensive Survey—vol. 3: Chemical and Biochemical Sensors, Part 2, Edited by W. Goepel, J. Hesse, J. N. Zemel, (VCH, 1992), Table of Contents pages only.
Sensors: A Comprehensive Survey—vol. 7: Mechanical Sensors, Part 2, Edited by W. Goepel, J. Hesse, J. N. Zemel, (VCH, 1994), Table of Contents pages only.
Y. Kinouchi et al., "Fast in vivo Measurement of Local Tissue Impedances Using Needle Electrodes", Med. Biol. Eng. Comput. 35(9):486-492, 1997—Abstract only.
R. Pethig, "Dielectric and Electronic Properties of Biological Materials", John Wiley & Sons, 1979, Cover and Table of Contents pages only.
S. Grimnes et al., "Bioimpedance and Bioelectricity Basics" Academic Press, Cover and Table of Contents pages only.
K. S. Cole, "Membranes, Ions and Impuses: A Chaper of Classical Biophysics", 1968, Cover and Tabe of Contents pages only.

* cited by examiner

TISSUE-CHARACTERIZATION SYSTEM AND METHOD

FIELD OF THE INVENTION

The present invention is generally in the field of medical devices, and relates to local tissue characterization system and method.

BACKGROUND OF THE INVENTION

A large number of techniques and sensors are available today for tissue characterization, for example, to determine the presence of abnormal tissue, such as cancerous or pre-cancerous tissue. These may be incorporated into hand-held probes or miniature probes, adapted for insertion into a body lumen or for use in minimally invasive surgery.

The use of suction, for engaging a medical instrument to a tissue, is known. For example, U.S. Pat. No. 5,927,284, to Borst, entitled, "A Method and Apparatus for Temporarily Immobilizing a Local Area of Tissue" whose disclosure is incorporated herein by reference, describes temporarily immobilizing a local area of heart tissue to permit surgery on a coronary vessel in that area without significant deterioration of the pumping function of the beating heart. The local area of heart tissue is immobilized to a degree sufficient to permit minimally invasive or micro-surgery on that area of the heart. A suction device is used to accomplish the immobilization. The suction device is coupled to a source of negative pressure. The suction device has a series of suction ports on one surface. Suction through the device causes suction to be maintained at the ports. The device is shaped to conform to the surface of the heart. Thus, when the device is placed on the surface of the heart and suction is created, the suction through the ports engages the surface of the heart. The suction device is further fixed or immobilized to a stationary object, such as an operating table or a sternal or rib retractor. Thus, the local area of the heart near the suction device is temporarily fixed or immobilized relative to the stationary object while suction is maintained. In this fashion, the coronary artery may be immobilized, even though the heart itself is still beating so that a bypass graft may be performed. In addition, the suction device may be used in either a conventional, open-chest environment or in a minimally-invasive, endoscopic environment.

Additionally, U.S. Pat. No. 6,728,565, to Wendlandt, entitled, "Diagnostic Catheter Using a Vacuum for Tissue Positioning" whose disclosure is incorporated herein by reference, describes the use of a diagnostic catheter, associated with a vacuum source, for attaching a sensor to a tissue surface. The method includes inserting a catheter with a sensor at its distal end into the body of a patient, applying suction through the catheter, to draw tissue into a predetermined sensing position for the sensor, and analyzing the tissue with the sensor. The degree of vacuum may be adjusted, so that only the required amount of force is used to maintain contact between the sensor or sensors and the tissue being analyzed.

SUMMARY OF THE INVENTION

There is a need in the art in a novel technique for local tissue characterization providing an automatically-activated process of engagement between a sensor/probe and the tissue, namely systems and methods enabling a reproducible static and automatic contact and release between the sensor/probe and the tissue, ensuring a reliable and effective tissue-characterization.

There is provided in accordance with some embodiments of the present invention a tissue measuring system which includes a probe, such as an extracorporeal, hand-held probe, having a sensor configured to measure one or more parameters indicative of one or more states of the tissue site; and a control unit associated with a vacuum source (pump) for providing suction to the probe. The control unit is connectable to the probe and is configured and operable to selectively activate the probe to carry out a measuring process (probe operation in a "measure mode") upon detecting a desired attachment (desired suction condition created by said vacuum source) between the probe and the tissue. The desired attachment is a condition in which a predetermined required degree of attachment has been achieved.

The probe is capable of selectively operating in either a scan mode, which includes attaching the probe to a tissue site using, for example, a pump and an attachment controller utility, and a measure mode which includes activating a mechanism, for example a mechanical mechanism for enabling a tissue characterization measurement process at the tissue site.

According to some embodiments of the present invention, the system may switch from the scan mode to the measure mode, thus enabling tissue characterization at the tissue site, by the at least one characterization sensor. In consequence, the accuracy and reproducibility of the characterizing process is improved. Additionally, the system may also provide a probe with a capability to detach from the tissue site, following the completion of a tissue characterization measurement.

The transfer between "scan" to "measure", and vice versa, is automated and does not require any user intervention. The transfer between modes is self regulated, and may be, for example, activated following changes of a vacuum level, for example in proximity to the probe. Additionally, when employed, the detachment of the probe is automated and does not require any user intervention.

Thus, the invention provides for automatic operation of a tissue measurement system based on automatic detection of a degree of attachment of the probe to the tissue site. More specifically, the control unit operates the probe to implement a 'scan' mode by setting the vacuum level at the distal end of the probe to a certain pressure. The probe is placed against the tissue site to be characterized, and is brought in contact with a tissue. The control unit identifies whether the probe is attached or fixed to the tissue, or generally whether a required degree of contact between the probe and the tissue is achieved or not. For example, bringing the probe closer to the tissue site affects a pressure level, or an optical signal change at the respective site, and changes in the pressure level or optical signal level are identified by the control unit (which utilizes an appropriate utility associated with a pressure or optical sensor and preprogrammed with a certain pressure/optical signal threshold corresponding to the required degree of contact). If the control unit identifies the existence of the required degree of attachment between the probe and the tissue, the control unit operates the probe to measure mode and to carry out a measurement process. To this end, the control unit may operate an attachment module carried by the probe to provide an effective contact between the probe and the tissue. If the scan mode does not result in the required degree of attachment between the probe and the tissue, the control unit generates instructions to user to place the probe again against the tissue.

There is thus provided according to one aspect of the invention, a measurement system for use in characterizing a tissue, the system comprising:

i. a probe adapted for operating in either a scan mode or a measure mode, said probe comprising:
   a) a sensing module comprising one or more sensors and configured and operable to measure one or more parameters indicative of one or more states of the tissue; and
   b) an attachment module configured and operable to enable selective operation of said probe in either one of the scan mode and the measure modes; and
ii. a control unit configured and operative to selectively operate the probe in either one of the scan and measure modes.

In some embodiments of the invention, the attachment module is shiftable between different configurations thereof corresponding to the modes of the probe.

In some embodiments of the invention, the attachment module is shiftable between different positions thereof corresponding to different degrees of attachment between the probe and the tissue.

The control unit is configured and operative to identify the degree of attachment between the probe and the tissue, to thereby selectively operate the probe in either one of the scan and measure modes.

As indicated above, in some embodiments of the invention the system includes a vacuum system connected to the probe. The vacuum system includes a vacuum source for providing suction to the probe, and a controller utility connectable to the vacuum source and configured and operable by a processor of the control unit to operate the probe in either one of the scan and measure modes. The vacuum system may or may not be a constructional part of the control unit.

The attachment module is preferably configured and operable to provide an effective contact between the probe and the tissue, and may also be operable to maintain the effective contact condition for a predetermined time period.

Preferably, the control unit is configured to automatically regulate the probe from the scan mode to the measure mode. This is preferably implemented upon detecting existence of a required degree of attachment between said probe and the tissue.

In some embodiments of the invention, the probe is manually regulated from the scan mode to the measure mode, by a user.

In some embodiments of the invention, the vacuum system is configured and operable to selectively provide a first vacuum level during the scan mode and a second vacuum level during the measure mode. The vacuum system may include one or more vacuum sensors configured to measure the suction level in proximity to the probe.

In some embodiments of the invention, the system may also selectively provide the probe operation in a release mode. In this case, the processor of the control unit may be configured to regulate the vacuum system from the measure mode to the release mode.

According to another broad aspect of the invention, there is provided a probe for use in characterizing a tissue, the probe comprising: a) a sensing module comprising one or more sensors and configured and operable to measure one or more parameters indicative of one or more states of the tissue; and b) an attachment module configured and operable to enable the operation of said probe on either one of the scan mode and the measure modes.

The probe may be configured as one of the following: an extracorporeal device, an intracorporeal device, a device adapted for use on a portion of subcutaneous tissue, and a device adapted for use on a portion of an intracorporeal tissue during an open surgery. Considering the probe configuration as an intracorporeal device, this may be one selected from the following: a device configured for minimally invasive surgery; a device configured for insertion via a trocar valve; a device configured for insertion via body orifice to a body lumen for use on a portion of inner lumen wall; a device adapted for percutaneous insertion to a body lumen for use on a portion of inner lumen wall; a device adapted for insertion via body orifice to a body lumen, for further penetrating the lumen for use on a portion of an intracorporeal tissue outside the lumen.

According to yet another broad aspect of the invention, there is provided a control unit for use in a measurement system for tissue characterization measurements, the control unit comprising a communication utility for communicating with a probe of the measurement system, and a processor utility operable to identify a degree of attachment between the probe and a tissue under measurements to selectively operate the probe in either one of a scan and measure modes.

The invention according to its yet further broad aspect provides a method for use in characterizing a tissue site, the method comprising: controlling the operation of a sensing module located within a probe, to selectively shift the sensing module from a scan mode into a measure mode, upon detecting existence of a predetermined attachment condition between the sensing module and the tissue site.

In some embodiment of the invention, during the scan mode, the attachment condition is characterized by a change in a first vacuum level between the probe and the tissue site, different from a second vacuum level maintained during the measure mode. Typically, the second vacuum level is lower than the first vacuum level.

According to yet another aspect of the invention, there is provided a method for use in characterizing a tissue site, the method comprising:

providing a probe comprising a sensing module, which comprises at least one sensor configured to measure one or more parameters indicative of one or more states of the tissue;

providing a vacuum system comprising a vacuum source for providing suction to the probe, and an attachment controller utility connectable to the vacuum source, said attachment controller utility being configured and operable to be regulated by a processor to selectively operate the probe in either one of a scan mode and a measure mode;

activating the vacuum system to operate the probe in the scan mode;

bringing the probe to the tissue site; and placing the probe against the tissue site, thereby adjusting the probe to the measure mode to enable the measurement by the sensor of the one or more parameters indicative of one or more states of the tissue at the tissue site.

DESCRIPTION OF THE DRAWINGS

In order to understand the invention and to see how it may be carried out in practice, embodiments will now be described, by way of non-limiting example only, with reference to the accompanying drawings, wherein.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well known features may be omitted or simplified in order not to obscure the present invention.

Some embodiments of the present invention are directed to a system and device for examining a substance, such as the tissue, in order to differentiate the examined substance from other substances according to the dielectric properties of the examined substance.

The present invention relates to tissue characterization. It will be appreciated that the term "tissue" refers to a skin, a body lumen, or an incision surface; either an arbitrary incision surface, or an incision surface contouring an organ.

Embodiments of the present invention are aimed at achieving effective contact, which is a contact level of at least 95%. Preferably, the contact level is greater than 98%. More preferably, the contact level is more closer to 100%-contact, namely 99.5%, and even 99.8% contact.

Additionally, in accordance with embodiments of the present invention, which relate to sensors, operating with a certain wavelength λ, the effective contact may be further defined as a contact, for which an average distance $t_1$ between the sensor and the tissue while in contact is at least a few times less than the wavelength λ, for example $t_1 < \lambda/3$, and preferably, $t_1 < \lambda/10$, and more preferably, $t_1 < \lambda/100$.

Additionally or alternatively, the effective contact may be defined in absolute terms. Accordingly, the average distance $t_1$ is less than 500 Angstroms, preferably the average distance $t_1$ is less than 50 Angstroms, and more preferably, the average distance $t_1$ is less than 5 Angstroms.

Figure 1:
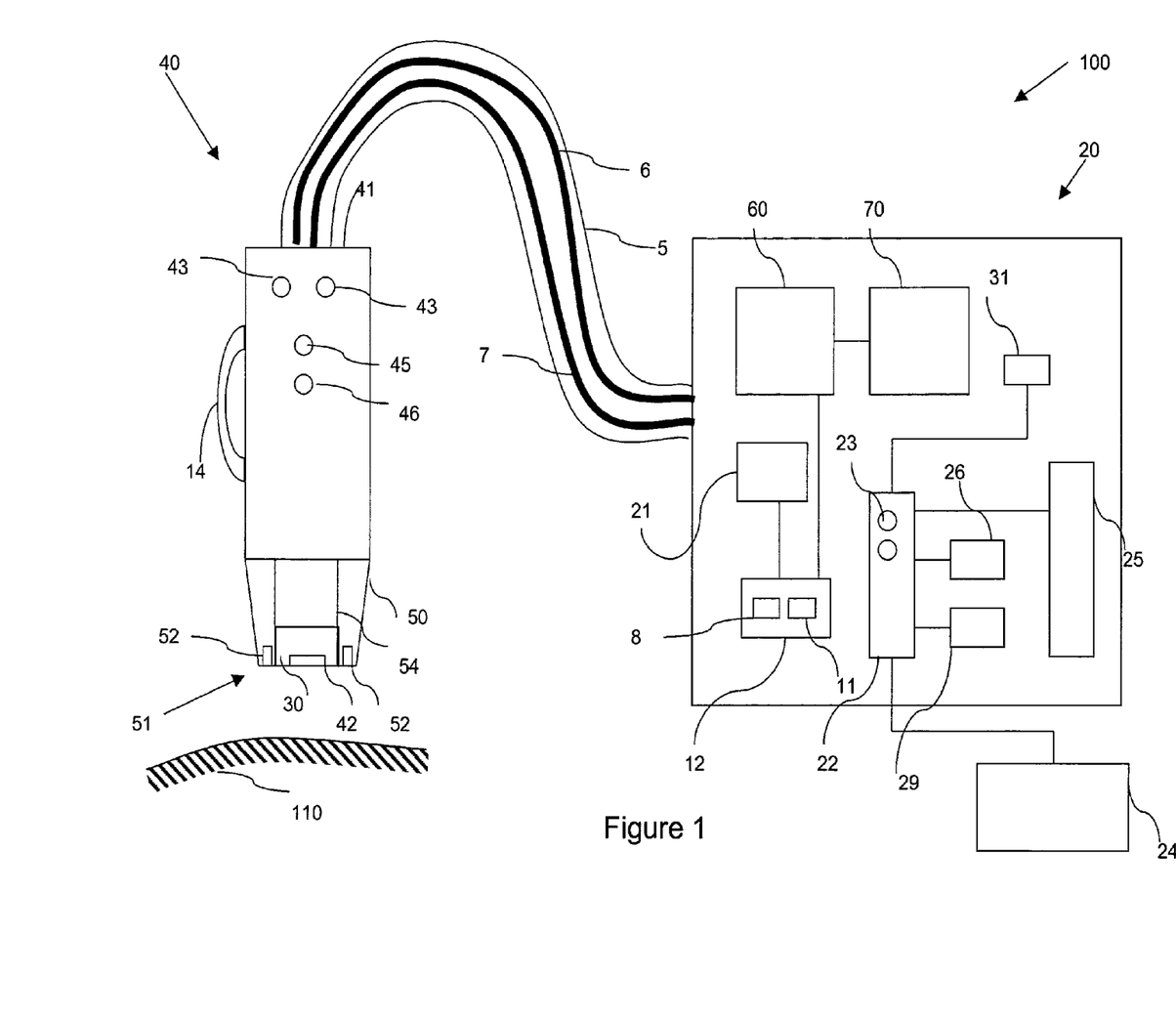
FIG. 1 schematically illustrates a system for measuring tissue parameters, in accordance with some embodiments of the present invention.

Reference is made to FIG. 1, which shows a schematic diagram of a system 100 for tissue characterization, in accordance with some embodiments of the present invention. The system 100 includes a probe 40 and a control unit 20 which is connectable to the probe 40 via communication cables 7 (as shown in the figure) or via wireless signal transmission, and via vacuum communication line 6. The control unit 20 is typically a computer system including inter alia a data processing and analyzing utility or Computer Processing Unit (CPU) 12, as well as data input and output utilities, communication utility, display, etc. Also provided in the control unit 20 is a controller utility 60 configured and operable for controlling an attachment between the relevant part of the probe 40 and a tissue 110; and a vacuum source, such as a pump 70. According to some embodiments of the present invention the probe 40 includes an attachment module 50 and a sensing module 30 including one or more sensors, such as a tissue characterization sensor 42.

The system 100 facilitates the probe to operate in the so-called "scan mode" and "measure mode". Additionally, the system may be configured to provide the probe 40 with a capability to detach from tissue 110, following the completion of a tissue characterization measurement.

In "scan mode", the system, namely the attachment controller utility 60 and vacuum source 70, operate for attaching the probe 40 to tissue 110, when the probe 40 is placed at contact with tissue 110. This attachment fixes the probe 40 to tissue 110, achieving a required degree of attachment. The required degree of attachment may be identified by indicating or sensing for example a pressure and/or optical signal change in proximity to the probe and/or the tissue.

When the required degree of attachment between the probe 40 and the tissue 110 is achieved e.g. in the "scan mode", the "measure mode" is activated, by activating a mechanism, for example a mechanical mechanism, that enables the performance of a tissue characterization measurement by sensor 42 at tissue site 110. The enabling of the performance of a tissue characterization measurement by sensor 42 at tissue site 110 may be, but not limited to, by the creation of an effective contact between the sensor 42 and the tissue 110.

The transfer between "scan" to "measure" mode, and vice versa, is automatically performed by the control unit 20 and does not require any user intervention. The transfer between modes is self regulated, and may be, for example, be activated following changes detected in the vacuum levels sensed at the attachment controller utility 60 and the probe 40, for example upon detecting the required degree of attachment between the probe and the tissue.

Additionally, when employed, the detachment of the probe is automated and does not require any user intervention.

According to some embodiments of the present invention, the sensing module 30 may be located at the distal end 51 of the probe 40, and may be part of, or connected to, the attachment module 50. According to some embodiments of the present invention, the characterization sensor 42 is a nonirradiative electromagnetic sensor for measuring the value of one or more parameters of the tissue site 110. The characterization sensor 42 may also be, for example, an optical sensor, an X-ray sensor, a radiofrequency (RF) sensor, a microwave (MW) sensor, an infrared thermography sensor, an ultrasound sensor, a magnetic resonance (MR) sensor, an impedance sensor, resistivity sensor, capacitance sensor, electric field sensor, magnetic sensor, radiation sensor, an acoustic sensor a thermistor or temperature sensor, a thermocouple, a biosensor, a chemical sensor, a radioactive-emission sensor, or a mechanical sensor.

The characterization sensor 42 may also be, for example, configured as disclosed in International Published Application WO 2006/103665 entitled "Electromagnetic sensors for tissue catechization" and in U.S. Pat. No. 7,082,325 entitled "Method and apparatus for examining a substance, particularly tissue, to characterize its type" which are assigned to the common assignee of the present application and which is hereby incorporated by reference. The WO 2006/103665 patent publication discloses a tissue sensing probe including a resonating element, formed as a conductive structure, and configured to be placed at an edge of a tissue site without penetrating into the tissue. The probe has a diameter-equivalent D, which defines a cross-sectional area of the resonating element on a plane substantially parallel to the edge. The resonating element is configured to resonate with a free-air wavelength in the range of about λ-10λ, wherein λ is at least about ten times the diameter-equivalent D. Upon receiving a signal in the range of about λ-10λ, the sensor induces electric and magnetic fields in a "near zone" in the tissue, the near zone being hemispherical with a diameter of substantially D, while causing negligible radiation in a "far zone", so that the tissue, in the near zone effectively functions as part of the resonating element, varying a resonating response to the sensor. The tissue, in the near zone is characterized by its electromagnetic properties by the resonating response of the sensor.

By way of another example, the sensor 42 may be a non-irradiative electromagnetic sensor for tissue characterization, for example, as taught in commonly owned U.S. Pat. No. 6,813,515, entitled "Method and system for examining tissue according to the dielectric properties thereof" whose disclosure is incorporated herein in its entirety by reference. This patent describes a non-irradiative electromagnetic sensor, which applies an electrical pulse to a tissue, thus generating an electrical fringe field in the zone of the tissue and producing a reflected pulse therefrom with negligible radiation penetrating into the tissue itself. The sensor detects the reflected electrical pulse and compares the electrical characteristics of the reflected electrical pulse with respect to the applied electrical pulse to provide an indication of the dielectric properties of the examined tissue.

The attachment module 50 includes one or more openings or orifices 52 located, for example at the distal end 51 of the probe 40, and a mechanism 54, such as a piston, for pressing the sensing module 30 and the characterizing sensor 42, against an external surface of the tissue 110. The attachment module 50 is configured and operable to enable the performance of a tissue characterization measurement by sensor 42 at tissue site 110, in a predetermined time period. As indicated above, the enabling of the performance of a tissue characterization measurement by sensor 42 at tissue site 110 may be, but not limited to, by the creation of an effective contact between the characterizing sensor 42 and the tissue 110. For example, in operation, suction is employed through the orifices 52 for thereby attaching tissue 110 to the probe distal end 51. Once the tissue 110 is attached to probe distal end 51, the mechanism 54 is activated to enable the performance of a tissue characterization measurement by sensor 42 at tissue site 110, in a predetermined time period.

The attachment module 50 may be similar to embodiments described in U.S. patent application Ser. No. 11/196,732, filed on Aug. 4, 2005, entitled "Device for forming an effective sensor-to-tissue contact", and in U.S. patent application Ser. No. 11/350,102, filed on Feb. 9, 2006, entitled "Tissue-Characterization Probe With Effective Sensor-To-Tissue Contact". Both these publications are assigned to the common assignee of the present application and are hereby incorporated by reference.

The probe 40 communicates with the control unit 20, namely with the attachment controller utility 60 and the pump 70 by a connection/communication cable 5 to thereby enable display of data, control, suction or other functions. The cable 5 may include at least one vacuum line or tube 6 to connect the attachment module 50 to the attachment controller utility 60 and further to the pump 70. The cable 5 may also include one or more wires and/or optical signal carriers 7 to connect the probe 40 to the control unit 20. In this case, as shown in FIG. 1, the proximal end 41 of the probe 40 is connected to the control unit 20, via the cable 5.

In accordance with the present invention, the probe 40 may be configured as one of the following: extracorporeal, handheld probe, for example having a handle 14 for easy carrying; to be employed for minimally invasive surgery, for example, for insertion via a trocar valve, or for another percutaneous insertion; an intracorporeal probe, adapted for insertion via body orifice to a body lumen, for characterizing a portion of inner lumen wall; an intracorporeal probe, adapted for percutaneous insertion to a body lumen, for characterizing a portion of inner lumen wall; an intracorporeal probe, adapted for insertion via body orifice to a body lumen, and for penetrating the lumen, for characterizing a portion of subcutaneous tissue; an intracorporeal probe, adapted for percutaneous insertion to a body lumen, and for penetrating the lumen, for characterizing a portion of subcutaneous tissue; an extracorporeal probe, adapted for characterizing a portion of skin.

The probe 40 may be an adapted for characterizing a portion of subcutaneous tissue, or on a portion of an intracorporeal tissue, during, for example, in open surgery.

According to some embodiments of the present invention the probe 40 may include one or more control buttons 43, one or more indicators, such as light sources LEDs 45 and 46. As indicated above, the control unit 20 typically includes a memory utility 21, the CPU 12 having a processor 8 and a memory 11, and a controller 22. The latter includes control buttons 23, and possibly also, data input units which may include a keypad or keyboard 26 or joystick 29, to input data to the CPU 12. The controller 22 may be in communication with a signal analyzer 25, an audio speaker 31 and possibly, with a display screen 24 to display relevant information to the operator. Alternatively, a hand-held device, or a laptop, as known, may be used. Other embodiments may have other configurations and capabilities.

The CPU 12 is configured to receive signals from the attachment controller utility 60 during delivery of the probe 40 to the tissue site to be treated. The CPU 12 analyzes the signals received from the controller utility 60 and determines whether or not the probe 40 is to be attached to the tissue site, whether or not the probe 40 is to be transferred to 'measure mode', measure one or more parameters indicative of one or more states of the tissue site or release the probe 40 from the tissue site.

According to some embodiments of the present invention, the CPU 12 is configured to regulate the vacuum level at the distal end 51 of the probe 40, in response to the vacuum level sensed by the attachment controller utility 60, in order to adjust this vacuum level to a desired value and keep said vacuum level for a predetermined time period which will enable a tissue characterization measurement by sensor 42 at tissue site 110, for example, by the creation of an effective contact between the characterizing sensor 42 and the tissue 110.

According to some embodiments of the present invention the system 100 is operated in at least two activation modes, a 'scan' mode and a 'measure' mode. During the 'scan' mode, for example, a first vacuum level is set at the orifices 52 at the distal end 51 of the probe 40, for example a vacuum pressure between about 0 and −20 kPA. During a 'measure mode', for example, a second vacuum level is set at the orifices 52 at the distal end 51 of the probe 40, a vacuum pressure which is higher than the vacuum pressure set during scan mode, for example, between about −20 kPA and −60 kPA. The control unit 20 is configured to regulate the vacuum level at the orifices 52 at the distal end 51 of the probe 40 when shifting the system operation between 'scan mode' and 'measure mode'.

Figure 2:
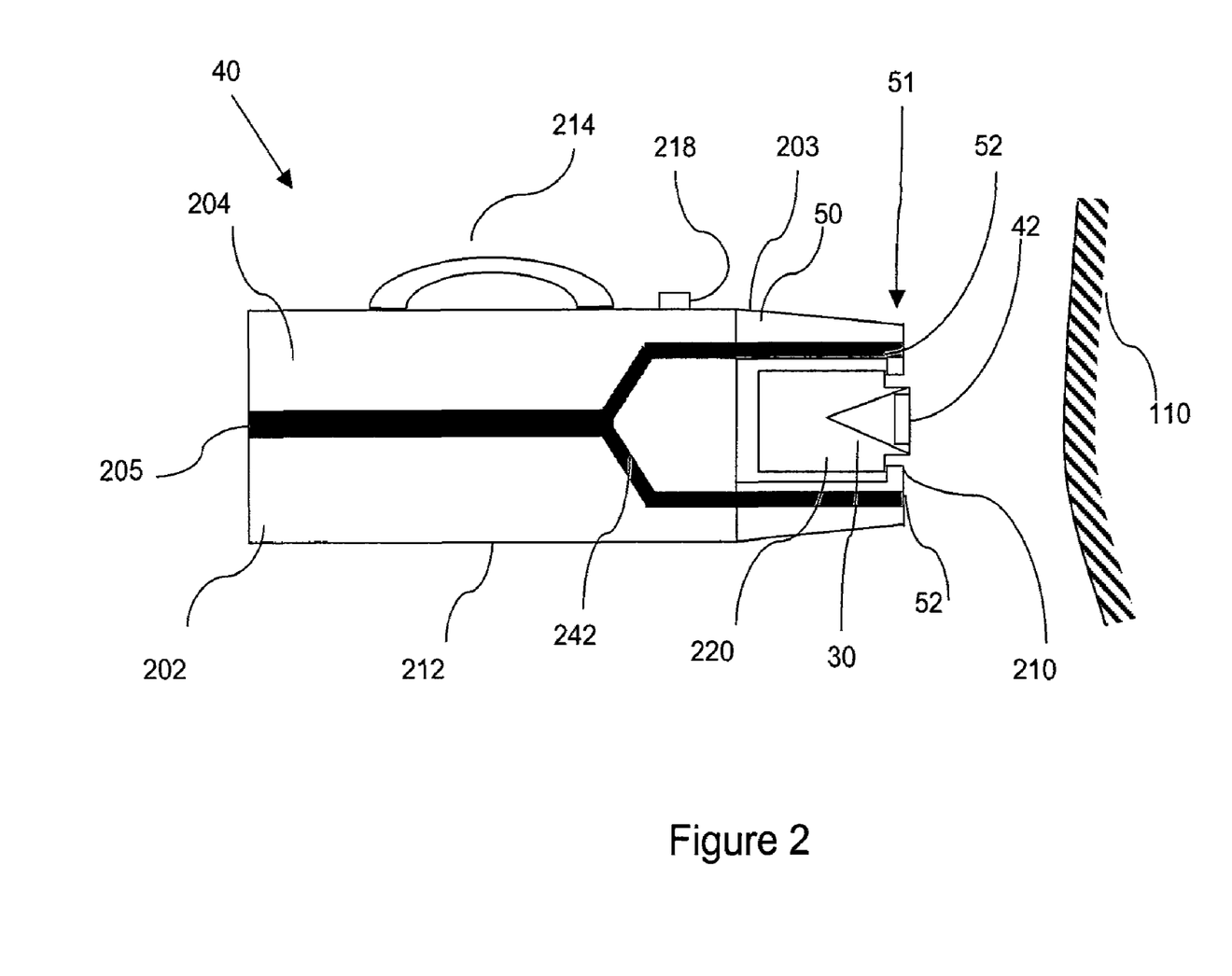
FIG. 2 schematically illustrates a probe for tissue characterization, in accordance with some embodiments of the present invention.

FIG. 2 schematically illustrates a cross-sectional view of the probe 40, in accordance with an embodiment of the present invention. The probe 40 is configured to form and maintain during a predetermined time period an effective sensor-to-tissue contact, to enable tissue characterization. The probe 40 includes a housing 212, carrying the attachment module 50 and the sensing module 30. In the present example, the housing 212 includes a first portion 202, forming a distal portion 204, adapted for hand gripping, and a second portion 203, containing the attachment module 50 and the sensing module 30. In accordance with this embodiment of the present invention, the probe 40 is a hand-held device including a handle 214, for easy carrying. The attachment module 50 includes an attachment element 210, located for example at a distal end 51. The attachment element 210 may be formed, for example as a ring, having inner and outer diameters, and/or may be shaped as a cone, other shapes may similarly be used.

According to some embodiments of the present invention, the attachment module 50 is associated with a first mechanism, such as the attachment element 210, designed for attaching tissue 110 to distal end of probe 40, for a predetermine time period. The attachment element 210 is provided with one or more orifices 52 connected for example to a duct system 242. The latter is configured and operable to provide air-pressure communication between the pump 70 and the attachment controller utility 60 of the control unit 20 (shown hereinabove in FIG. 1) and the attachment module 50 of the probe 40, for creating a negative pressure required to attach tissue 110 to the attachment element 210, by suction for a predetermined time period. A vacuum outlet 205 is adapted for connecting to the pump 70.

Additionally, the probe 40 may include a second mechanism, such as a piston 220, within second portion 203. Piston 220 may be connected to or may include the characterization sensor 42. Piston 220 is configured for selective deployed and retracted positions. According to some embodiments of the present invention, the piston movement, and/or position, from retracted to deployed state and vice versa, may be vacuum actuated. For deployment, the piston slides proximally and presses against tissue 110, thus achieving effective sensor-to-tissue contact between characterization sensor 42 and tissue the 110.

According to some embodiments of the present invention, the probe 40 may include at least one input device, such as a button 218, to input data to the CPU 12, for example, but not limited to, the name, the measured point or number of measurement for each measurement output.

Figure 3A:
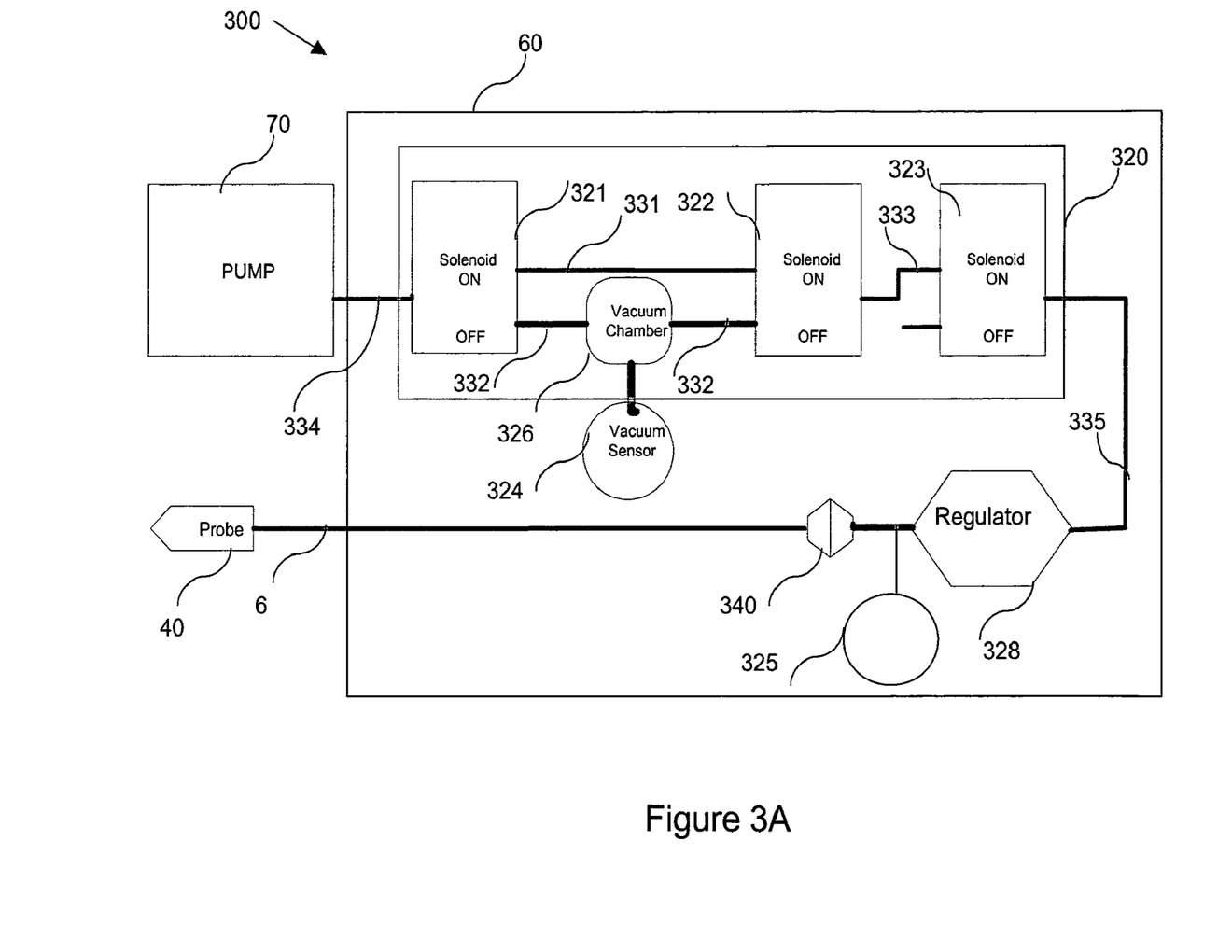
FIG. 3A is a block diagram of the components of the attachment control unit, in accordance with some embodiments of the present invention.

FIG. 3A shows a block diagram of the components of a vacuum system 300, in accordance with one embodiment of the present invention. The vacuum system 300 is configured to automatically switch the probe 40 modes from a 'scan' mode to a 'measure' mode, and vice versa, upon receipt of a signal from the CPU 12, thus, enabling an automatic static and reproducible tissue characterization measurement process of a tissue site. According to another embodiment of the present invention, the vacuum system 300 is also configured to automatically release the probe 40 from tissue site 110 (e.g. release mode) following the measurement process.

According to some embodiments of the present invention, the vacuum system 300 includes the attachment controller utility 60 which may be connected, for example via tube 334 to one or more pumps such as the pump 70. The pump 70 may be for example a 15D1150-101-1014 pump commercially available from GAST, or 7006-2,3E pump commercially available from THOMAS. The attachment controller utility 60 may include a connection controller 320 which may be connected via tube 335 to a vacuum sensor 325 and further to the probe 40. In operation, the pump 70 provides suction (vacuum pressure), via attachment controller utility 60, to the attachment module 50 in probe 40. The CPU 12 monitors the vacuum level at the distal end of the probe 40, measured by the vacuum sensor 325, and identifies when the level has changed or reached a threshold. If the pressure level is below a threshold pressure level the CPU 12 regulates the vacuum level at the probe distal end (e.g. transfer to "measure" mode). As a result, an automatic activation of a mechanism that enables the performance of a tissue characterization measurement by sensor 42 at tissue site 110, is applied by the connection controller 320, for a predetermined time. The connection controller 320 may also activate the disconnection of the probe 40 from the tissue site 110, following the completion of a tissue characterization measurement by sensor 42.

According to some embodiments of the present invention, the connection controller 320 includes one or more solenoids, such as V310-39-24VDC solenoids commercially available from Humphrey, or SVB18-M-S solenoids commercially available from Pisco, one or more flow controllers, such as, for example, JSU4(K) flow controller commercially available from Pisco, at least one sensor, such as a vacuum sensor 324, and a vacuum chamber 326. For example, volume of vacuum chamber 326 may be between about 10 cc and 1000 cc.

In the example of FIG. 3A, a first solenoid 321 is connected via a first tube 331 to a second solenoid 322. The vacuum chamber 326 and the first sensor 324 are connected via a second tube 332 to the first solenoid 321 and the second solenoid 322. The second solenoid 322 is connected to a third solenoid 323 via a third tube 333. Devices and systems as described herein may have other configurations and other sets of components. For example, according to some embodiments of the present invention, the second vacuum sensor 325 may be connected to the second solenoid 322 and the third solenoid 323.

According to some embodiments of the present invention each solenoid may for example be operated separately, by the CPU 12, to facilitate the transfer of the attachment controller utility 60 between at least two modes, for example, three different modes: scan, measure and release, as will be illustrated hereinbelow in conjunction with FIG. 4. For example, during the scan mode a direct path is open between the probe 40 and the pump, e.g. solenoids 321, 322 and 323 are on, applying a first vacuum level to the probe distal end. During the measure mode, there is a vacuum path between the vacuum chamber 326 and the probe 40, e.g. the first solenoid 321 and the second solenoid 322 are off and the third solenoid 323 is on, applying a second vacuum level to the probe distal end. During release mode the third solenoid 323 is off connecting the vacuum line of the probe distal end to atmospheric pressure.

The vacuum sensor 325 may be connected to a regulator 328 and a fluid trap unit 340, and may be part of the connection controller 320. According to some embodiments, the vacuum sensor 325 is located at the probe 40, for example at the distal end 51 thereof. The vacuum sensor 325 may be, for example, a VUS11-01-A sensor commercially available from Pisco, or a ZSE40-01-62 commercially available from SMC. The regulator 328 may be for example a IRV1000-F01 regulator commercially available from SMC, or a VR100 regulator commercially available from Koganei. The regulator 328 may be set to a vacuum level which is lower than the set vacuum level at the vacuum chamber 326, a level of between about −15 kPa and −55 kPa. This lower vacuum level ensures that a homogenous vacuum level is maintained during the activation of 'measure' mode. The fluid trap unit 340 is configured to isolate the probe 40 from the rest of the components of the vacuum system 300, e.g. for preventing fluid entering the probe 40 from reaching the rest of the components of the vacuum system 300, and of reaching the vacuum pump 70.

Figure 3B:
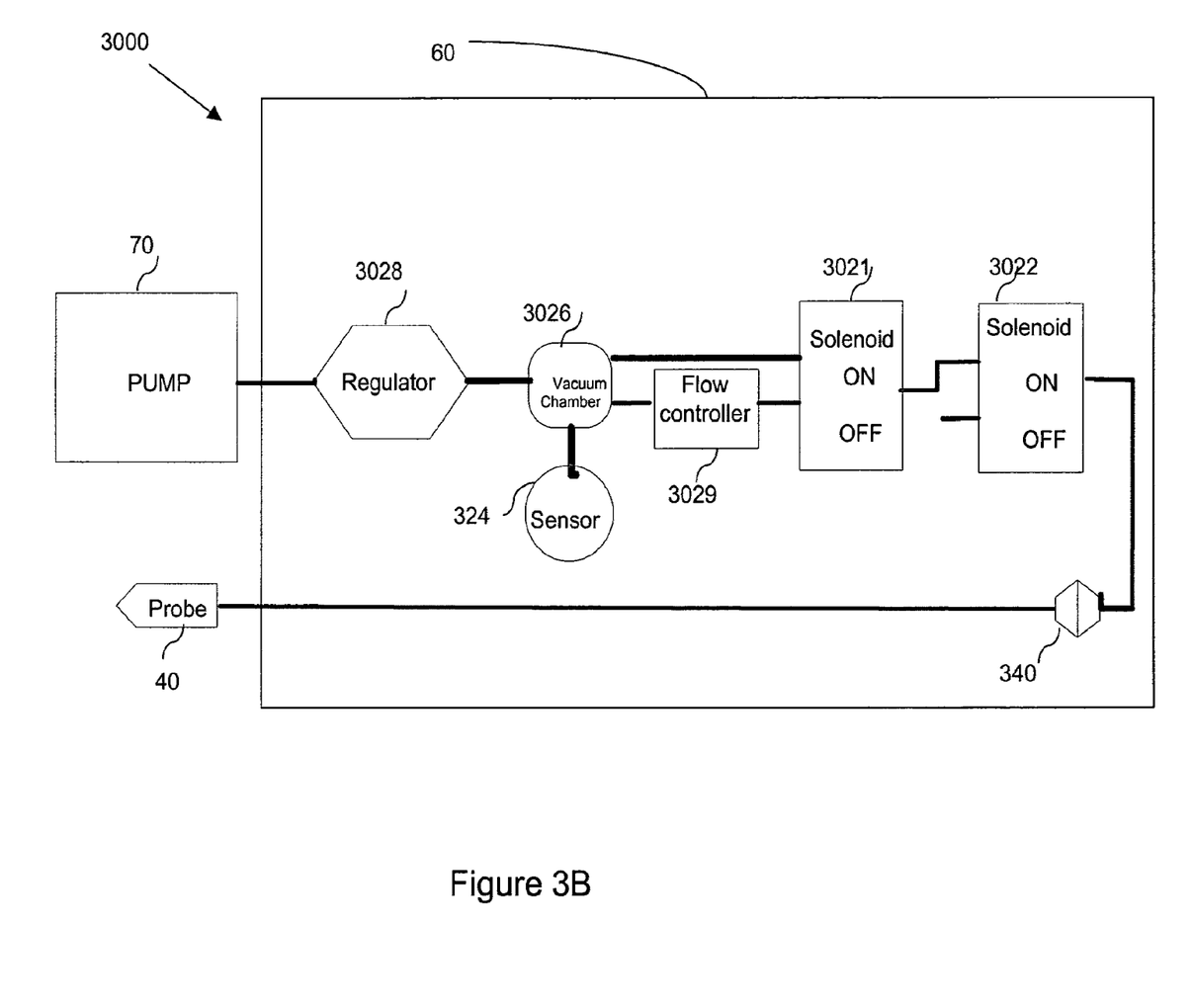
FIG. 3B is a block diagram of the components of the attachment control unit, in accordance with some other embodiments of the present invention.

FIG. 3B shows a block diagram of the components of a vacuum system 3000, in accordance with another embodiment of the present invention. The vacuum system 3000 is configured to automatically switch the probe 40 modes from a 'scan' mode to a 'measure' mode, and vice versa, upon receipt of a signal from the control unit 20 (from the CPU 12), thus, enabling an automatic static and reproducible tissue characterization measurement process of a tissue site. The vacuum system 3000 may also be configured to automatically release the probe 40 from tissue site (e.g. release mode) following the measurement process.

According to in the example of FIG. 3B, during the scan mode a vacuum path is open between the probe 40 and the pump 70, via a flow controller 3029, e.g. solenoid 3021 is off and solenoid 3022 is on, applying a first vacuum level to the probe distal end. The first vacuum level is determined by the set value of the flow controller. During the measure mode, there is a vacuum path between the vacuum chamber 3026 and the probe 40, e.g. solenoids 3021 and 3022 are on, applying a second vacuum level to the probe distal end. During release mode, solenoid 3022 is off connecting the vacuum line of the probe distal end to atmospheric pressure. In the embodiment shown in FIG. 3B, the regulator 3028 is set to vacuum level of 'measure' mode. This is also the vacuum level at the vacuum chamber 3026, as the pump 70 is constantly connected to the chamber. The homogenous vacuum level is maintained during the activation of 'measure' mode by the direct path kept between the pump 70, via the regulator 3028, and probe 40 during 'measure' mode.

In some embodiments of the present invention, the vacuum regulator may be substituted with a vacuum relief valve.

Figure 4:
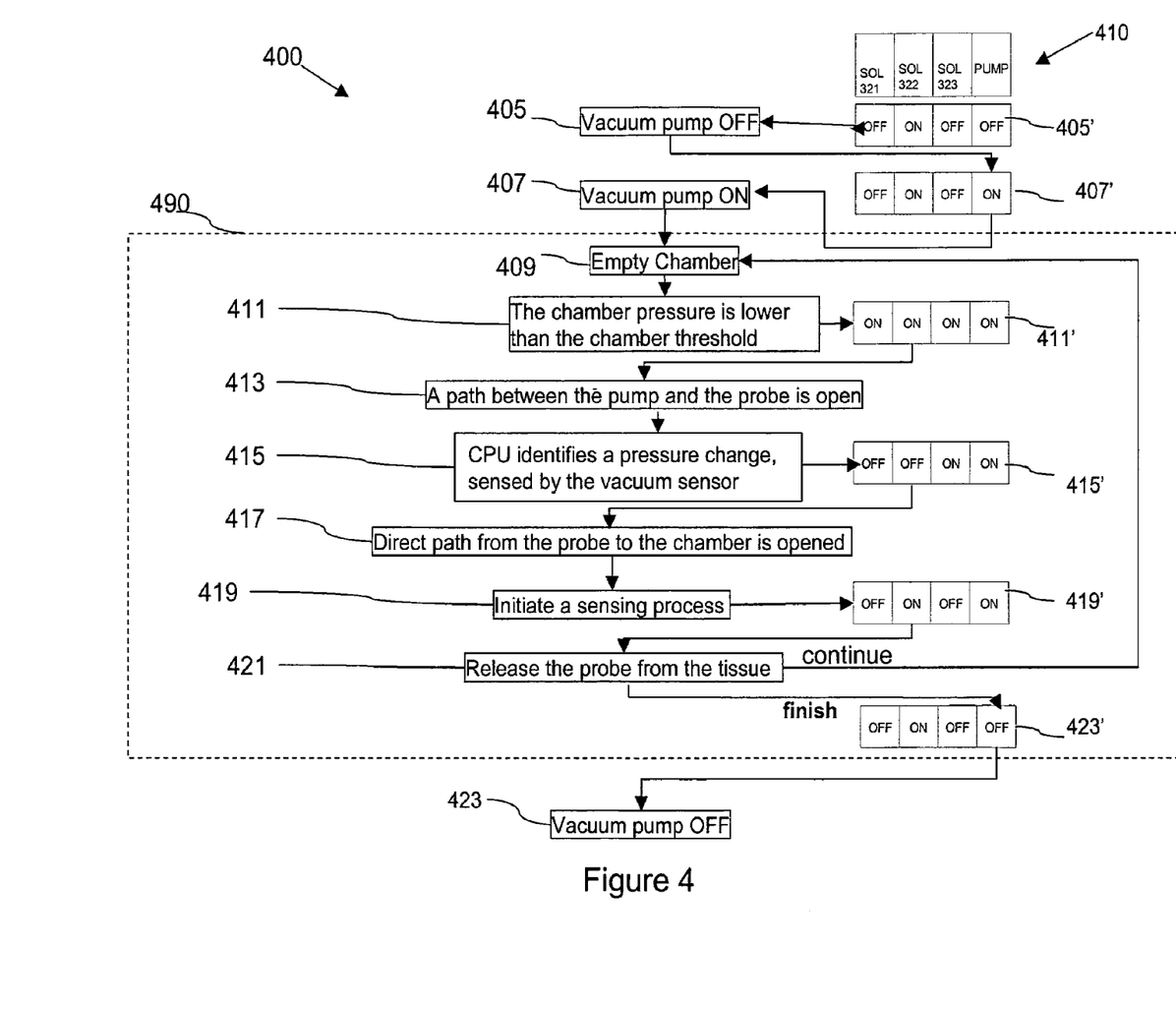
FIG. 4 shows a flowchart and a list of status conditions, in accordance with some embodiments of the present invention.

FIG. 4 exemplifies a flowchart 400, illustrating a measurement process including automatically regulating the vacuum level of the above-described system 100 during a 'scan' mode and a 'measure' mode, and a condition list 410 illustrating the state of the solenoids 321, 322 and 323 of the above-described vacuum system 300 and the pump 70 during each step of the measurement process. In step 405 the pump 70 is off, the third solenoid 323 and the first solenoid 321 are turned off while the second solenoid 322 is switched on (condition 405'), for example by the CPU 12. In step 407 the pump 70 is switched on while the first solenoid 321 and the third solenoid 323 are still off and the second solenoid 322 is still on (condition 407'), for emptying the vacuum chamber 326.

Thereafter, the measurement process enters a control cycle 490 which includes the following steps: In step 409 the vacuum chamber 326 is emptied by the pump 70, for example in approximately less than 5 sec-200 msec. The emptied chamber will be further used, in step 417, to switch the attachment controller utility 60 to measure mode, for a predetermined time period, and to enable the performance of a tissue characterization measurement by sensor 42, by, for example, utilizing the creation of effective contact between sensor 42 and tissue site 110. In step 411 the first vacuum sensor 324 indicates that the pressure level in the chamber 326 is lower than the chamber's set threshold, for example less than between about −20 kPa and −60 kPa, and a first signal is transmitted to the CPU 12. The CPU 12 receives the first signal and regulates the system 100 to the 'scan' mode by switching the first solenoid 321 and the third solenoid 323 on (condition 411'). In step 413 the system 100 is in a 'scan' mode e.g. a path between the pump 70 and the probe 40 is open producing a first vacuum level at the distal end 51 of the probe 40. The first vacuum level may be for example between about 0 and −20 kPa. The first vacuum level produced during scan mode is sufficient to attach the probe 40 to the tissue, but not to enable tissue characterization measurement by sensor 42 at tissue 110. During step 413 the probe 40 is physically brought proximally to tissue 110, for example, by hand. This initial, position of the probe is shown in FIG. 5A, where the probe is in a configuration of scan mode.

Figures 5A, 5B, 5C:
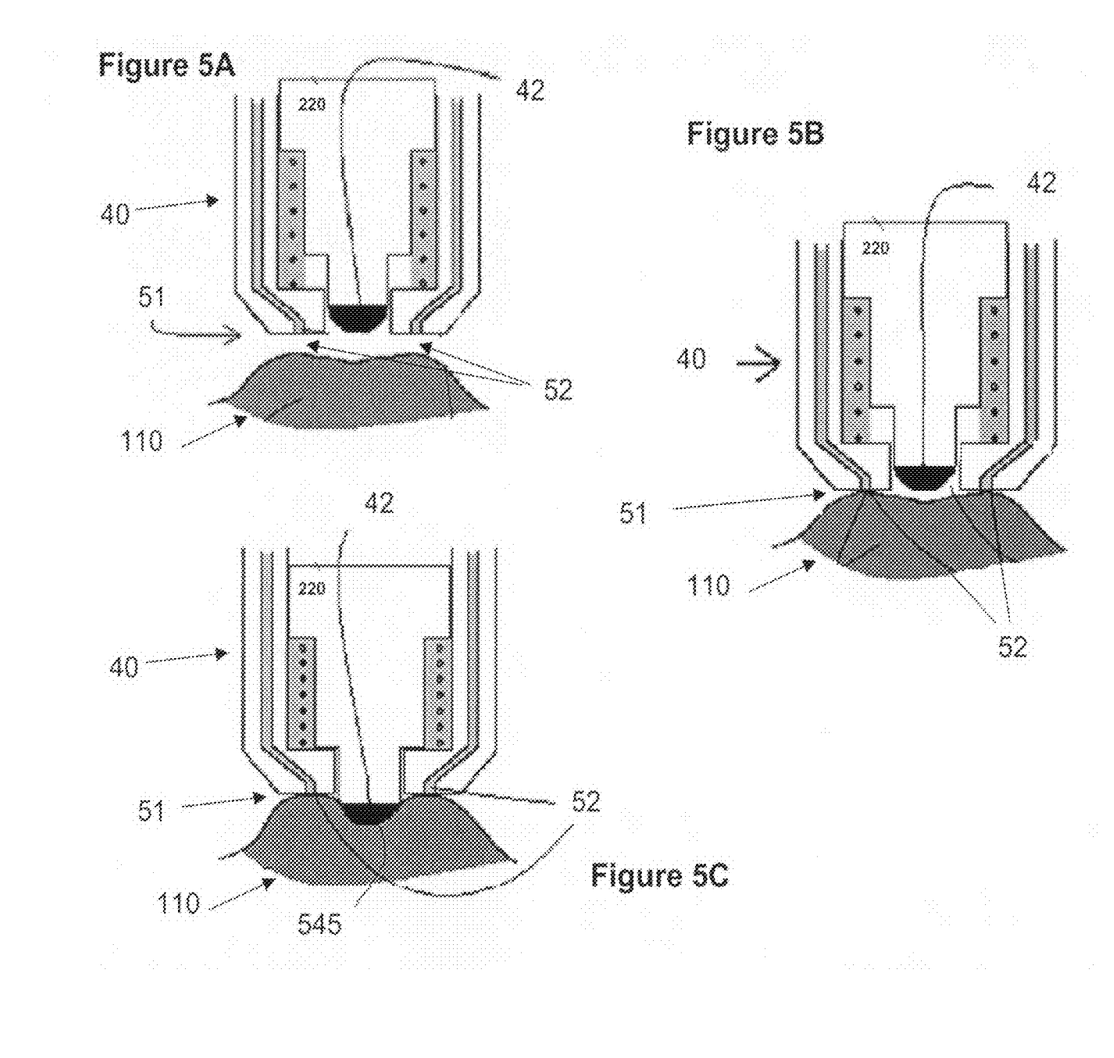
FIGS. 5A-5C schematically illustrate an example of the proximal end portion of a probe for forming effective sensor-to-tissue contact, during a 'scan' mode and 'measurement' mode in the operation of the probe, in accordance with the present invention.

Once the probe 40 is brought in contact with tissue 110, as shown in FIG. 5B, orifices 52 are sealed by the tissue 110, and thus probe 40 is attached to tissue 110. The vacuum level in scan mode is sufficient to attach the probe to the tissue, but not to activate the mechanism that enables achieving effective contact between sensor 42 and tissue 110. This is also shown in FIG. 5B, where the piston 220 is still in the retracted position. The sealing of orifices 52 by the tissue 110 results in a pressure drop in the vacuum line. As a result, the CPU 12 identifies a pressure change, sensed by the vacuum sensor 325 at the distal end 51 of the probe 40 (step 415), and regulates the system 100 from the 'scan' mode to the 'measure' mode. A pressure change may be defined as a pressure level at the distal end 51 of the probe 40, e.g. the required degree of attachment between the probe 40 and the tissue, which is lower than a threshold, for example lower than the −20 kPa and −60 kPa. During the 'measure' mode the CPU 12 regulates the pressure level at the distal end 51 of the probe 40 to be adjusted to a second vacuum level, of for example less than about −15 kPa and −55 kPa, by turning off the first solenoid 321 and the second solenoid 322 (condition 415'). Thereafter, a direct path between the distal end 51 of the probe 40 and the chamber 326 is open (step 417), activating the mechanism that enables the performance of a tissue characterization measurement by sensor 42, by, for example, achieving effective contact between the tissue 110 and the characterizing sensor 42. The activation of the mechanism is rapid, for example in less than 200 msec. For example, as shown in FIG. 5C, the probe is in a configuration of measure mode, resulting from the second vacuum pressure level which enables the deployment of the second mechanism 220, for pressing the characterization sensor 42 against tissue surface 110, forming substantially a single interface 545. Thus, effective sensor-to-tissue contact has been formed, substantially, as described, and for example tissue characterization may take place, by the characterization sensor 42. According to some embodiments of the present invention a regulator 328 may be used to ensure a constant and identical pressure level during the measurement process, e.g. during the measure mode. In step 419 the CPU 12 initiates a sensing or characterization process. According to some embodiments of the present invention the sensing process may be activated for a predetermined time, for example less than about 5 sec to 30 msec. After the sensing process is completed, the CPU 12 may activate in step 421 the release of the probe from tissue 110, and the return of the system to 'scan' mode by switching on the second solenoid 322 and turning off the third solenoid 323 (condition 419') letting atmospheric pressure to get into the probe, and as a result the probe is automatically released from the tissue. According to some embodiments of the present invention the probe is released from a tissue, for example in about less than 500 msec to 2 mesc. The process may return to step 409, for the initiation of another measurement cycle, which includes setting the solenoids position as shown in condition 407', as the process is continuously carried out in the control cycle 490, or may be completed in step 423 by turning off the pump (condition 423'). When the process is continuous, the probe may be kept released providing enough time for removing the probe 40 from the tissue, even though the controller utility 60 is ready again in scan mode.

Figure 6:
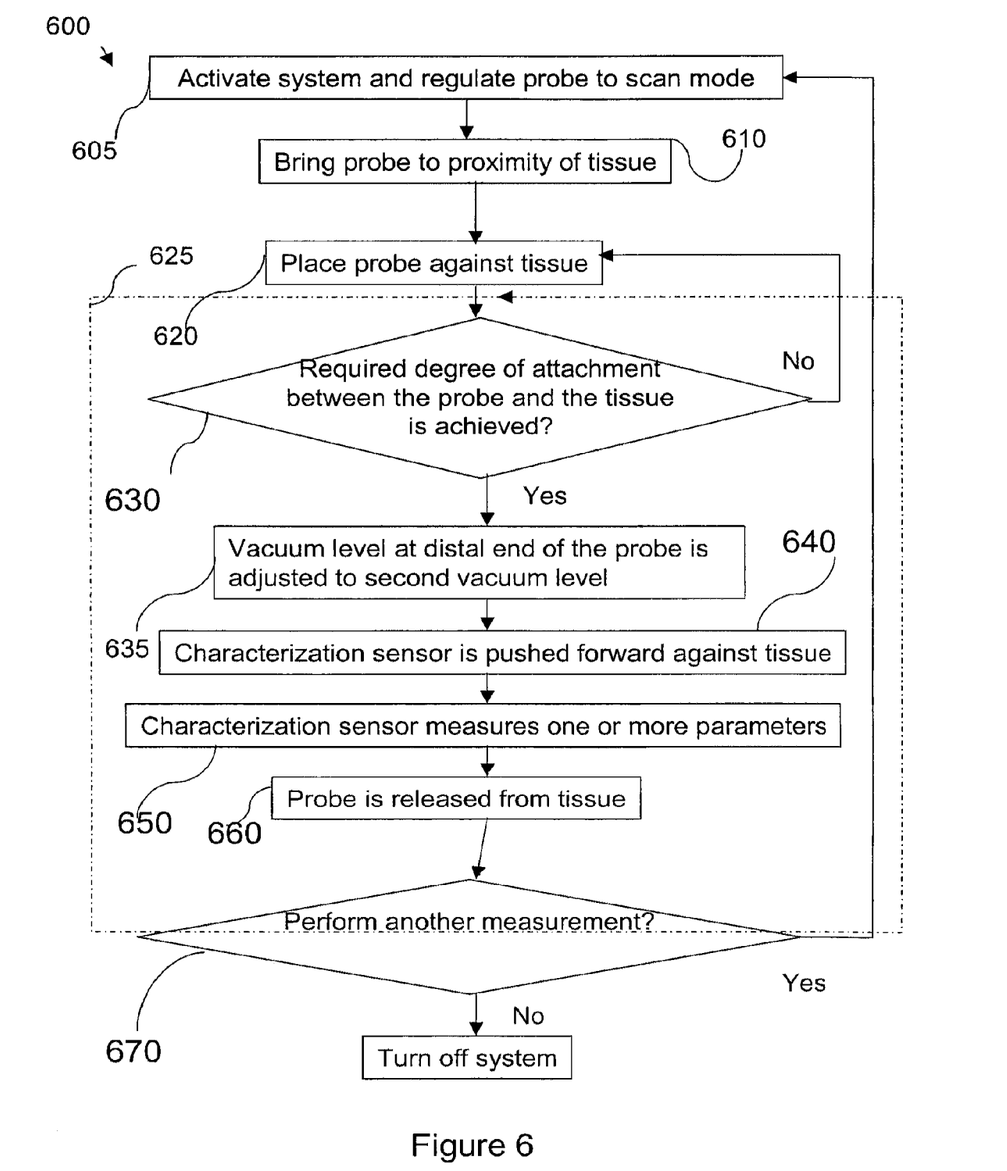
FIG. 6 is a flowchart of a method for tissue measurement in accordance with some embodiments of the method of the invention.

Reference is now made to FIG. 6 exemplifying a flowchart 600 of a method for measuring parameters of a tissue site. In step 605 the system 100 is activated. The CPU 12 regulates the probe 40 to a 'scan' mode state which includes setting the vacuum level at the distal end 51 of the probe 40, e.g. at the orifices 52, to a low negative pressure which may be between about 0 and −20 kPa. According to some embodiments of the present invention, the pump 70 may be switched on, or the system may be switched to a 'scan' mode by a user, or automatically, or by holding and/or moving the probe 40. In step 610, the probe 40, which is preferably a hand-held probe, is physically brought proximally to a tissue site to be characterized, for example, by hand. The tissue site to be characterized may be located on the body surface, or may be an internal body site, or may be a tissue site exposed by incision during surgery. If the site to be measured is internal, the probe 40 may be inserted into the body through a body orifice, such as the mouth, nostril or anus. Alternatively, the probe 40 may be introduced percutaneously through an incision in the skin. In step 620, the probe 40 is placed against the tissue site to be characterized, for example, inside a lumen, at a tissue incision site, or on the surface of part of the body. During step 620 the probe 40 is brought in contact with a tissue portion and is attached to tissue, as shown in FIG. 5B, and as a result the pressure at the orifices 52 at the proximal end of the probe 51 drops and an automatic control cycle 625 is initiated, for example by the CPU 12. In step 630, it is determined whether the required degree of attachment between the probe 40 and the tissue is achieved e.g. whether the pressure level in proximity to the probe 40 is below a predetermined threshold. If the required degree of attachment between the probe 40 and the tissue was not achieved, e.g. pressure level is above the predetermined threshold, the user is instructed to place the probe again against the tissue (step 620). If the required degree of attachment between the probe 40 and the tissue is achieved, e.g. the pressure is below the predetermined threshold, the CPU 12 regulates the probe to a 'measure' mode. In step 635 the CPU adjusts the vacuum level at the distal end 51 of the probe, for example to a second vacuum level of less than about −15 kPa to −55 kPa. As a result of this second vacuum level, in step 640, a mechanism operates to enable the performance of a tissue characterization measurement by sensor 42, for example, by achieving effective contact between the tissue 110 and the characterizing sensor 42. This is shown, for example, in FIG. 5C, where the probe 40 is in a configuration of measurement mode, resulting from the second vacuum pressure level, set in step 635, which enables the deployment of the second mechanism (piston) 220, for pressing the characterization sensor 42 against tissue surface 110, forming substantially a single interface 545. Thus, effective sensor-to-tissue contact has been formed, substantially, as described. In step 650 one or more parameters indicative of one or more states of the tissue are measured, for example by the characterization sensor 42. Following the completion of the measurement in step 650, in step 660 the CPU 12 automatically releases the probe 40 from the tissue site. In step 670, the control unit operates to check whether additional measurements are to be performed or not (e.g. in response to operator's input), and if not the system is turned off in step 680 or if additional measurements are to be performed, e.g. no action is taken by the user, CPU 12, further regulates the probe back to the 'scan' mode, for the initiation of another measurement. The regulation back to 'scan' mode may be delayed for a predetermined time, to enable removing the probe from the tissue.

According to some embodiments of the present invention, the user may receive an indication regarding the status mode of the probe 40. The indication may be displayed, for example, on the probe 40 using for example the light sources 45 and 46, e.g. red LED—scan mode, green LED—measure mode, or on the display screen 24. The indication regarding the status mode of the probe 40 may also be an audio indication.

It will be appreciated that the technique of the present invention may be used without release mode.

It will also be appreciated that the invention could also be used for sensing and characterizing other types of substances, for example, in situ characterization of polymer and elastomer products and coatings.

It will also be appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All patent publications mentioned in this specification are herein incorporated in their entirety by reference into the specification, to the same extent as if each individual publication was specifically and individually indicated to be incorporated herein by reference. In addition, citation or identification of any reference in this application shall not be construed as an admission that such reference is available as prior art to the present invention.

The invention claimed is:

1. A measurement system for use in characterizing a tissue, the system comprising:
   i. a probe adapted for operating in either a scan mode or a measure mode, said probe comprising:
      a) a sensing module comprising one or more sensors and configured and operable to measure one or more parameters indicative of one or more states of the tissue; and
      b) an attachment module configured and operable to provide attachment between the probe and tissue under measurements during the probe operation in the scan mode and the measure mode;
   ii. a control unit configured and operative to identify a degree of attachment between the probe and the tissue and selectively operate the probe in either one of the scan and measure modes; and
   iii. a vacuum system configured and operable to selectively provide a first vacuum level during the scan mode and a second vacuum level during the measure mode.

2. The system according to claim 1, wherein the attachment module is configured and operable to be shiftable between different configurations thereof corresponding to the modes of the probe.

3. The system according to claim 1, wherein the attachment module is configured and operable to be shiftable between different positions thereof corresponding to the different degrees of attachment between the probe and the tissue.

4. The system according to claim 1, configured and operable to selectively operate the probe in one of the following modes: scan mode, measure mode, and a release mode.

5. The system according to claim 1, wherein the attachment module is configured and operable to provide an effective contact between said one or more sensors and the tissue.

6. The system according to claim 5, wherein the attachment module is configured and operable to maintain the effective contact between said one or more sensors and the tissue for a predetermined time period.

7. The system according to claim 1, wherein the attachment module is configured and operable to maintain the measure mode for a predetermined time period.

8. The system according to claim 1, wherein the control unit is configured to automatically regulate the probe from the scan mode to the measure mode.

9. The system according to claim 4, wherein the control unit is configured to regulate a vacuum system for providing suction to the probe from the measure mode to the release mode.

10. The system according to claim 1, wherein the control unit is configured to automatically regulate the probe from the scan mode to the measure mode, upon detecting existence of a required degree of attachment between said probe and the tissue.

11. The system according to claim 1, wherein the probe is configured to be manually regulated from the scan mode to the measure mode by a user.

12. The system according to claim 1, configured and operable to provide attachment of the probe to the tissue during the scan mode.

13. The system according to claim 1, wherein the attachment module comprises a mechanism configured to attach the one or more sensors to the tissue.

14. The system according to claim 13, wherein said mechanism comprises one or more orifices.

15. The system according to claim 1, wherein the attachment module comprises a mechanism enabling the measurement by the sensor.

16. The system according to claim 15, wherein said mechanism is a piston.

17. The system according to claim 1, wherein the vacuum system is connected to said probe and comprises:
  a vacuum source for providing suction to the probe; and
  a controller utility connectable to the vacuum source and configured and operable by a processor of the control unit to operate the attachment module during the scan mode and the measure mode.

18. The system according to claim 17, wherein the vacuum system is configured and operable to selectively provide a first vacuum level during the scan mode and a second vacuum level during the measure mode.

19. The system according to claim 17, wherein the vacuum system comprises at least one vacuum sensor configured to measure the suction level in proximity to the probe.

20. The system according to claim 17, wherein the processor is configured to regulate the vacuum system from the scan mode to a measure mode.

21. The system according to claim 17, wherein the processor is configured to regulate the vacuum system from the measure mode to a scan mode.

22. The system according to claim 17, wherein the attachment controller utility comprises one or more solenoids, one or more vacuum sensors, and one or more vacuum chambers.

23. The system according to claim 17, wherein the vacuum system comprises a regulator configured and operable to provide a substantially constant pressure level.

24. The system according to claim 17, wherein the vacuum system comprises a flow controller configured to restrict the pressure level.

25. The system according to claim 17, wherein the vacuum system comprises a fluid trap unit configured to isolate the probe from the vacuum system.

26. A control unit for use in a measurement system for tissue characterization measurements, the control unit comprising a communication utility for communicating with a probe of the measurement system, and a processor utility operable for controlling an attachment between the probe and a tissue under measurcmcntsmeasurement and upon identifying a desired attachment operating the probe to switch from a scan mode to a measure mode to thereby allow tissue characterization measurements.

27. A method for use in characterizing a tissue site, the method comprising: controlling the operation of a sensing module located within a probe, to selectively shift said sensing module from a scan mode into a measure mode, upon detecting existence of a predetermined attachment condition between the sensing module and the tissue site.

28. The method according to claim 27, wherein, during said scan mode, said attachment condition is characterized by a change in a first vacuum level between the probe and the tissue site, different from a second vacuum level maintained during the measure mode.

29. The method according to claim 28, wherein said second vacuum level is lower from said first vacuum level.

30. A method for use in characterizing a tissue site, the method comprising:
  providing a probe comprising a sensing module, which comprises at least one sensor configured to measure one or more parameters indicative of one or more states of the tissue;
  providing a vacuum system comprising a vacuum source for providing suction to the probe, and an attachment controller utility connectable to the vacuum source, said attachment controller utility being configured and operable to be regulated by a processor to selectively operate the probe in either one of a scan mode and a measure mode in accordance with a degree of attachment between the probe and the tissue;
  activating the vacuum system to operate the probe in the scan mode;
  bringing the probe to the tissue site; and
  placing the probe against the tissue site, thereby adjusting the probe to the measure mode to enable the measurement by the sensor of the one or more parameters indicative of one or more states of the tissue at the tissue site.

31. The method according to claim 30, wherein the vacuum system is configured to bring about, in a predetermined time, an effective contact between the sensor and the tissue.

32. The method according to claim 30, wherein the probe is configured to be operated in a release mode.

33. The method according to claim 30, wherein during said scan mode said vacuum system is producing a first vacuum level.

34. The method according to claim 30, wherein during said measure mode said vacuum system is producing a second vacuum level.

35. The method according to claim 34, wherein said second vacuum level is lower from said first vacuum level.

* * * * *